(12) United States Patent
Ryu et al.

(10) Patent No.: US 9,230,705 B2
(45) Date of Patent: Jan. 5, 2016

(54) PORTABLE LATENT FINGERPRINT DEVELOPING APPARATUS

(71) Applicant: KOREIT CO., LTD., Chungcheongbuk-do (KR)

(72) Inventors: Eal Young Ryu, Daejeon (KR); Won Sik Oh, Gyeonggi-do (KR); Hee Yeong Hwang, Daejeon (KR); Sung Bin Yim, Daejeon (KR); Nack Do Sung, Daejeon (KR); Yong Bok Choi, Chungcheongnam-do (KR); Kyung Mo Sung, Daejeon (KR); Kang Su Lim, Chungcheongnam-do (KR); Sung Kug Lee, Daejeon (KR)

(73) Assignee: Nack-Do Sung, Daejeon (KR)

( * ) Notice: Subject to any disclaimer, the term of this patent is extended or adjusted under 35 U.S.C. 154(b) by 559 days.

(21) Appl. No.: 13/707,686

(22) Filed: Dec. 7, 2012

(65) Prior Publication Data

US 2014/0085444 A1 Mar. 27, 2014

(30) Foreign Application Priority Data

Sep. 26, 2012 (KR) .......... 10-2012-0107031

(51) Int. Cl.
*G21K 5/08* (2006.01)
*H04N 5/222* (2006.01)
*G06K 9/00* (2006.01)
*A61B 5/117* (2006.01)

(52) U.S. Cl.
CPC .............. *G21K 5/08* (2013.01); *G06K 9/00013* (2013.01); *H04N 5/222* (2013.01); *A61B 5/1172* (2013.01)

(58) Field of Classification Search
CPC ........ A61B 5/1172; A61B 5/117; B44F 1/10; G03F 1/68; G03F 1/0038; G21K 5/00; G21K 5/08; G06K 9/00013; C23C 14/246; B05C 5/02
USPC ...................... 118/31.5, 715, 726; 427/1, 145; 250/492.1; 430/10
See application file for complete search history.

(56) References Cited

U.S. PATENT DOCUMENTS

| 7,323,207 | B2 | 1/2008 | Nichols et al. | |
|---|---|---|---|---|
| 8,272,343 | B1 * | 9/2012 | Weaver et al. | ............... 118/31.5 |
| 2010/0040764 | A1 * | 2/2010 | Schwartz | ........................... 427/1 |
| 2010/0310755 | A1 | 12/2010 | Attar | |
| 2011/0090541 | A1 | 4/2011 | Harper | |
| 2012/0141669 | A1 * | 6/2012 | Stones | ........................ 427/145 |

FOREIGN PATENT DOCUMENTS

| JP | 2009-056084 A | 3/2009 |
|---|---|---|
| JP | 2011-188969 A | 9/2011 |
| KR | 10-2006-0011368 A | 2/2006 |
| KR | 10-2011-0012799 A | 2/2011 |

* cited by examiner

*Primary Examiner* — Laura Edwards
(74) *Attorney, Agent, or Firm* — Rabin & Berdo, P.C.

(57) ABSTRACT

Disclosed is a portable latent fingerprint developing apparatus capable of visibly checking out an external shape of a finger print by using an UV LED lamp, after a fine spray of a fingerprint developing liquid is conducted by using a vibrator and providing the corresponding fingerprint image to an external terminal, after it is photographed by a camera.

16 Claims, 8 Drawing Sheets

Effect of fingerprint developing

Conventional art

Present invention

PORTABLE LATENT FINGERPRINT DEVELOPING APPARATUS

BACKGROUND OF THE INVENTION

1. Field of the Invention

The present invention relates to a portable latent fingerprint developing apparatus. More particularly, the present invention relates to a portable latent fingerprint developing apparatus capable of visibly checking out an external shape of a finger print by using an UV LED lamp, after a fine spray of a fingerprint developing liquid is conducted by using a vibrator and providing the corresponding fingerprint image to an external terminal, after it is photographed by a camera.

2. Description of the Prior Art

According to the supply the state-of-the-art digital equipment such as a color printer or a scanner etc., the counterfeit money has been rapidly increased all over the world.

Also, since the counterfeit money discrimination device, which is used all over the world, is very expensive and it is uncomfortable to use, there is a limit on the supply thereof.

In the meantime, according to data from the Bank of Korea, when 50,000 won large bills were issued in 2009, the probability of the counterfeit thereof is increased by the counterfeiters.

With the development of the office automation equipment, which is a computer peripheral equipment, various digital color output equipment (copy machine or printer) having superior resolution (400 dpi to 1,440 dpi) have been appeared. Accordingly, since banks and securities can be easily copied, various crimes such as the counterfeit thereof etc. have been increased.

In order to solve these problems, the anti-forgery techniques of the bills are studied. In the anti-forgery techniques, there are a silver coin, a silver wire, a fluorescent color fiber, an optically variable printing material, an intaglio printing, a fluorescent ink, an intaglio latent image, a fine lettering, and a line printing etc.

In the counterfeit discernment method of the techniques for counterfeit prevention applied to the banks and the securities, if it shines the bright light on the silver part, the special patterns or characters are appeared. Also, the face value, the characters, and the structure etc. can be checked out through a convex touch in the intaglio printing parts.

In case of the fluorescent ink, an ultraviolet light and an infrared light are irradiated on the banks by using an ultraviolet fluorescent lamp and an infrared fluorescent lamp, so that the inherent color of the fluorescent material is emitted, thereby discriminating the true currency and the fake currency. Also, in case of the magnetic ink applied to the banks and the securities, it judges the existence of the magnetic properties by means of the magnet, thereby discriminating the true currency and the fake currency.

However, after it makes an exquisite counterfeit using the color output equipment (copy machine or printer), since the anti-forgery techniques such as the silver coin, a partially exposing silver wire, a fluorescent color fiber, an optically variable printing material, an intaglio printing etc. are imitated and faked by means of a transparent ink, a powdered silver ink, an aluminum thin film, and an embossing machine etc., it is hard for the ordinary person to tell with the naked eye that the banks and the securities are counterfeit.

Also, the banks, the securities, and the identification can be faked by the international forgers.

Since the ordinary persons are always exposed to this risk, it is necessary to judge the true or the false of the security products such as the banks, the securities, and the copy prevention paper. Also, it is difficult for the ordinary person to use the precision machinery used in the bank, since it has problems in terms of a size, a cost, and a management thereof.

Accordingly, the development of a multifunctional counterfeit bill detector for judging the true or the false of various security products regardless of time and place has been required.

Also, in case of a fingerprint detector used in the scene of the crime, since a fingerprint developing liquid is applied or sprayed, the fingerprint is collapsed or disappeared. Accordingly, since it is a quite cumbersome to shine the UV LED light again after the spraying of the fingerprint developing liquid, it is hard to rapidly collect the evidence at the scene of the crime.

SUMMARY OF THE INVENTION

Accordingly, the present invention has been made to solve the above-mentioned problems occurring in the prior art, and an object of the present invention is to provide a portable latent fingerprint developing apparatus capable of visibly checking out an external shape of a finger print by using an UV LED lamp, after a fine spray of a fingerprint developing liquid is conducted by using a vibrator and providing the corresponding fingerprint image to an external terminal, after it is photographed by a camera.

Another object of the present invention is to provide a portable latent fingerprint developing apparatus in that a fine spray can be conducted without spraying or applying the fingerprint developing liquid and it shines the UV LED light simultaneously with the spraying of the fingerprint developing liquid, so that it can be sprayed in a wide space and the fingerprint image can be directly detected.

Another object of the present invention is to provide a portable latent fingerprint developing apparatus capable of providing convenient portability and storage to users.

In order to accomplish these objects, there is provided a portable latent fingerprint developing apparatus, including: a case; a developing reagent tank for storing a developing liquid therein; a vibrator for vibrating the developing liquid supplied from the developing reagent tank according to a control of a controller and spraying fine droplets through a fine droplet spraying device; the fine droplet spraying device for discharging the fine droplets formed by the vibrator to outside; an UV lamp for irradiating an UV light on an object; and the controller for controlling the vibrator.

Preferably, the UV lamp and the fine droplet spraying device face in the same direction so as to spray the fine droplets of the developing liquid and irradiate the UV light of the UV lamp toward the same area, thereby detecting the fingerprint image simultaneously with the spray thereof.

Preferably, the developing reagent tank includes a separate stopper formed at a rear portion of the case so as to store the fingerprint developing liquid therein and open and close the developing reagent tank.

Preferably, the fine droplet spraying device includes a plurality of small apertures formed at a front portion of the case so as to discharge the fine droplets formed by the vibrator to outside.

Preferably, the UV lamp is formed on the periphery of the fine droplet spraying device at regular intervals and includes a plurality of UV LEDs for irradiating the UV light on the object.

Preferably, the portable latent fingerprint developing apparatus further includes a camera for automatically photographing a fingerprint when the fingerprint is developed on the object and storing a fingerprint image in a memory unit according to a control of the controller; and the memory unit for storing the fingerprint image photographed by the camera therein.

Preferably, the portable latent fingerprint developing apparatus further includes a fingerprint image discriminating unit for recognizing and discriminating the fingerprint images so as to obtain the images through the camera continually operated and automatically recognize the fingerprint images, thereby storing the fingerprint images in the memory unit.

Preferably, the portable latent fingerprint developing apparatus further includes an USB port for transmitting the fingerprint image to an external terminal.

Preferably, the portable latent fingerprint developing apparatus further includes a spraying switch for spraying the fine droplet.

Preferably, if the spraying switch is pressed, the UV lamp is simultaneously operated.

In order to accomplish these objects, there is provided a portable latent fingerprint developing apparatus, including: a case; a developing reagent tank formed on a rear portion of the case so as to store a developing liquid therein; a vibrator for vibrating the developing liquid supplied from the developing reagent tank according to a control of a controller and spraying fine droplets through a fine droplet spraying device; the fine droplet spraying device formed on a front of the case so as to discharge the fine droplets formed by the vibrator to outside; an UV lamp formed on the periphery of the fine droplet spraying device at regular intervals so as to irradiate an UV light on an object; a camera for automatically photographing a fingerprint when the fingerprint is developed on the object and storing a fingerprint image in a memory unit according to a control of the controller; the memory unit for storing the fingerprint image photographed by the camera therein; an USB port for transmitting the fingerprint image to an external terminal; a spraying switch for spraying the fine droplet and operating the UV lamp; and the controller for controlling the vibrator, the fine droplet spraying device, the UV lamp, the camera, the memory unit, the USB port, and the spraying switch.

Preferably, the UV lamp is electrically connected to the camera.

Preferably, the portable latent fingerprint developing apparatus, further includes a power supplying unit formed on one side of the rear portion thereof so as to supply a power thereto.

Preferably, during operating of the spraying switch, the controller obtains the corresponding signal and transmits the operation signal to the fine droplet spraying device and the UV lamp so as to irradiate the UV light on the object simultaneously with the spray thereof and then, an operation signal is transmitted to the camera by means of the controller, thereby photographing the fingerprint image, when the fingerprint on the object is recognized.

Preferably, at least one UV lamp includes a plurality of short wavelength lamps for generating a short wavelength wave and a plurality of long wavelength lamps for generating a long wavelength wave.

Preferably, the portable latent fingerprint developing apparatus further includes a camera switch for operating the camera.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, an exemplary embodiment of the present invention will be described in detail with reference to the accompanying drawings.

Figure 1:
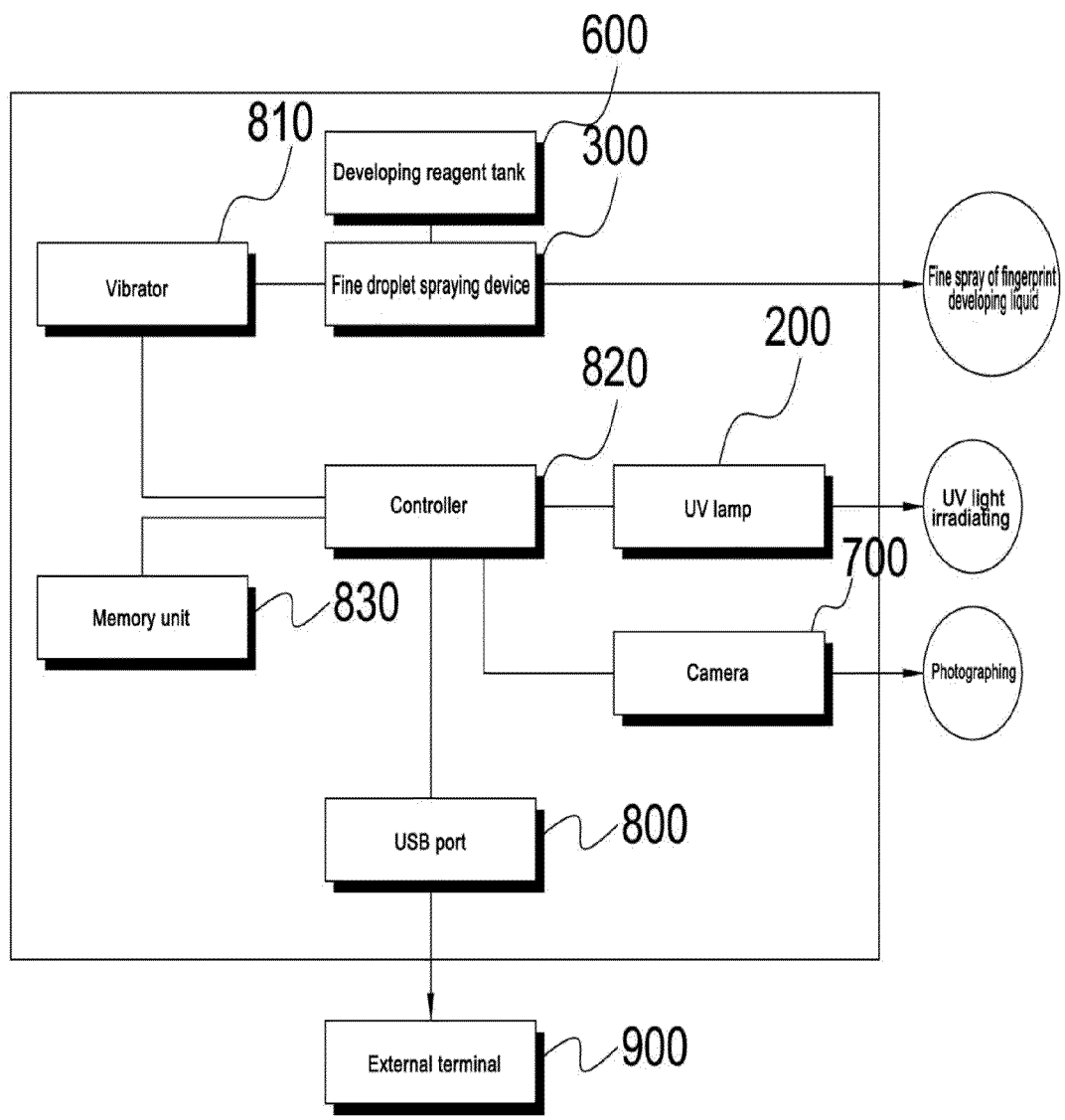
FIG. 1 is a block diagram illustrating a portable latent fingerprint developing apparatus according to one embodiment of the present invention.
Figure 2:
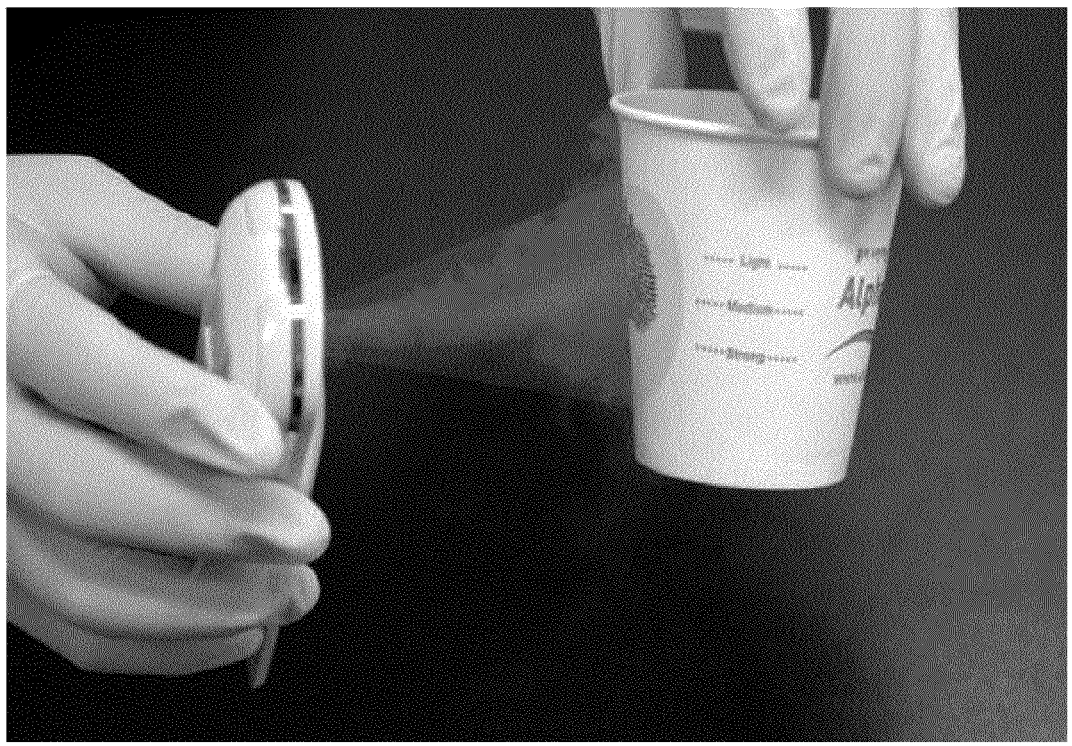
FIG. 2 is an example view illustrating a status of checking out a latent fingerprint with the naked eye during the operation of a UV lamp simultaneously with a spray by using a portable latent fingerprint developing apparatus according to one embodiment of the present invention.
Figure 3:
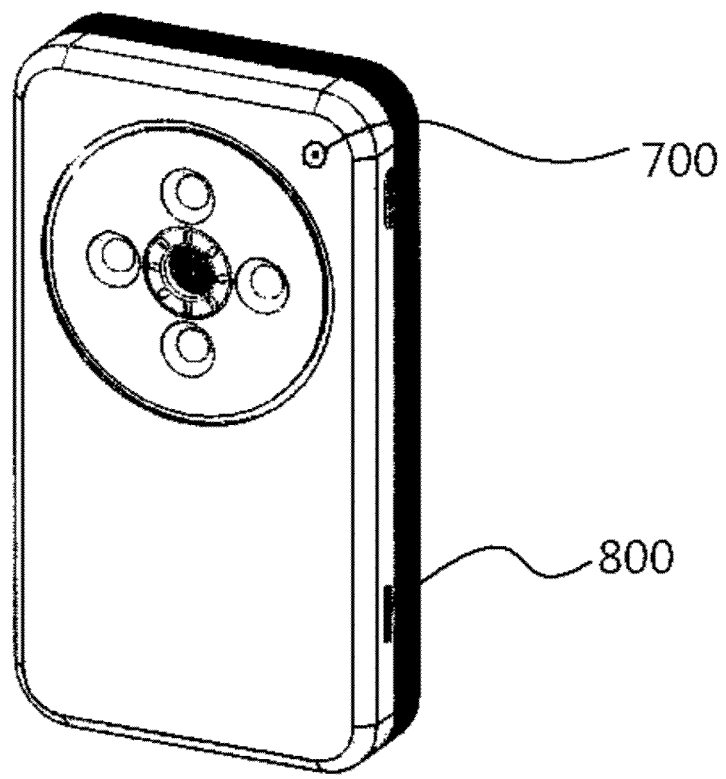
FIG. 3 is a perspective view illustrating a front portion of a portable latent fingerprint developing apparatus according to one embodiment of the present invention.
Figure 4:
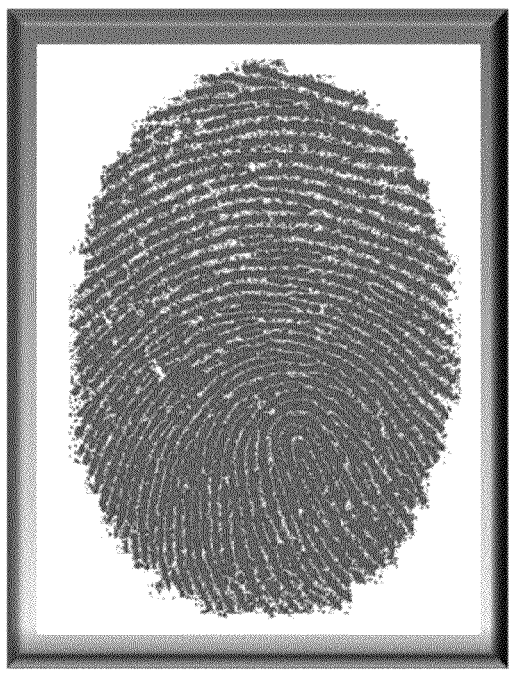
FIG. 4 is an example view illustrating a fingerprint developing effect for comparing a portable latent fingerprint developing apparatus according to one embodiment of the present invention with a conventional art.
Figure 4:
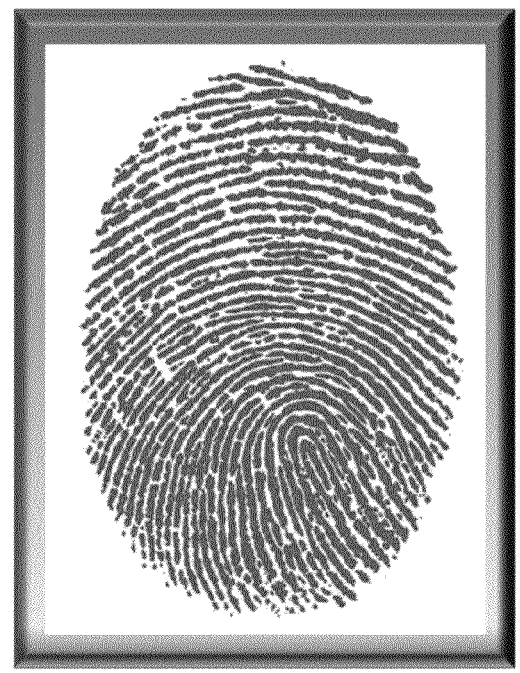
Figure 5:
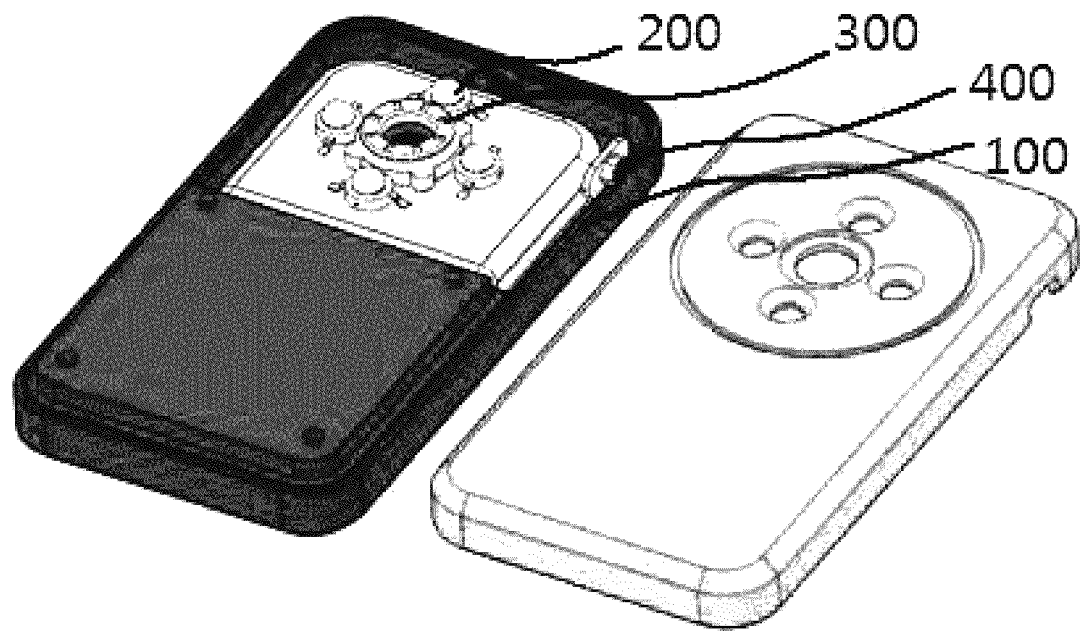
FIG. 5 is another perspective view illustrating a front portion of a portable latent fingerprint developing apparatus according to one embodiment of the present invention.
Figure 6:
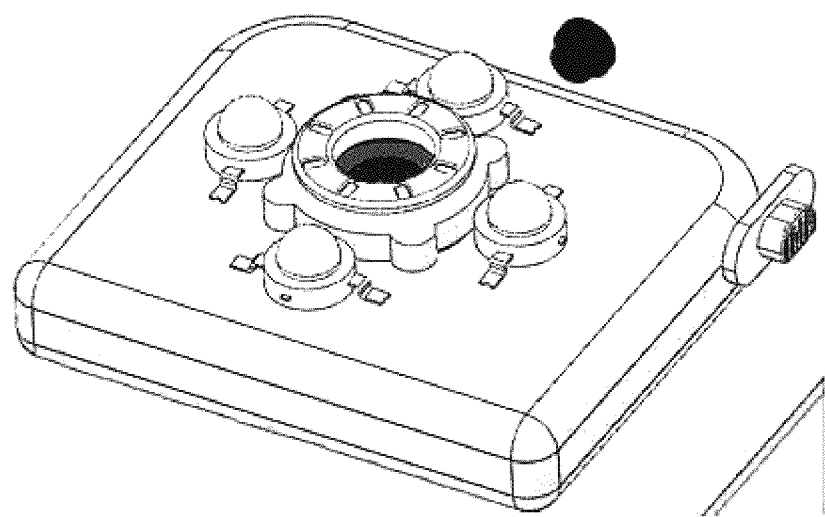
FIG. 6 is an enlarged perspective view illustrating a fine droplet spraying device and an UV lamp of a portable latent fingerprint developing apparatus according to one embodiment of the present invention.
Figure 7:
FIG. 7 and FIG. 8 are perspective views illustrating a rear portion of a portable latent fingerprint developing apparatus according to one embodiment of the present invention.
Figure 8:
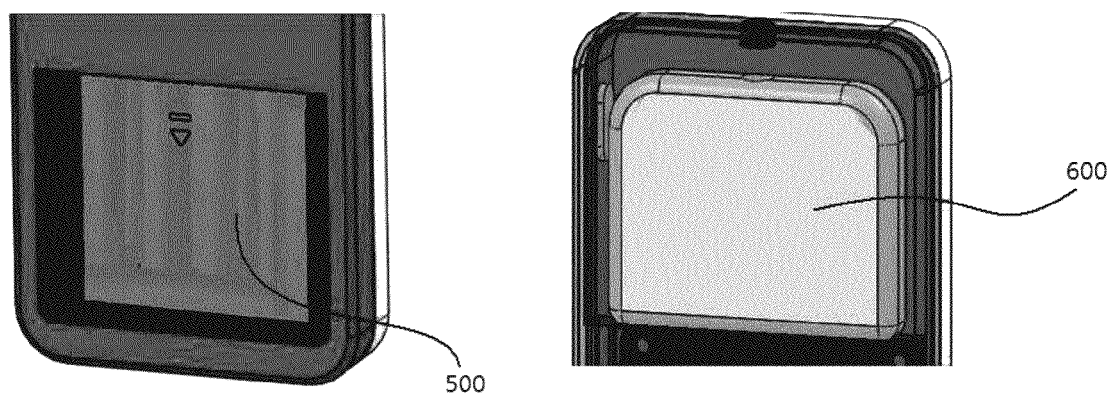

FIG. 1 is a block diagram illustrating a portable latent fingerprint developing apparatus according to one embodiment of the present invention, FIG. 2 is an example view illustrating a status of checking out a latent fingerprint with the naked eye during the operation of a UV lamp simultaneously with a spray by using a portable latent fingerprint developing apparatus according to one embodiment of the present invention, FIG. 3 is a perspective view illustrating a front portion of a portable latent fingerprint developing apparatus according to one embodiment of the present invention, FIG. 4 is an example view illustrating a fingerprint developing effect for comparing a portable latent fingerprint developing apparatus according to one embodiment of the present invention with a conventional art, FIG. 5 is another perspective view illustrating a front portion of a portable latent fingerprint developing apparatus according to one embodiment of the present invention, FIG. 6 is an enlarged perspective view illustrating a fine droplet spraying device and an UV lamp of a portable latent fingerprint developing apparatus according to one embodiment of the present invention, and FIG. 7 and FIG. 8 are perspective views illustrating a rear portion of a portable latent fingerprint developing apparatus according to one embodiment of the present invention.

As shown in FIG. 1, the portable latent fingerprint developing apparatus according to one embodiment of the present invention includes:

a case 100;

a developing reagent tank 600 formed on a rear portion of the case 100 so as to store a developing liquid therein;

a vibrator 810 for vibrating the developing liquid supplied from the developing reagent tank 600 according to a control of a controller 820 and spraying fine droplets through a fine droplet spraying device 300;

the fine droplet spraying device 300 formed on a front of the case 100 so as to discharge the fine droplets formed by the vibrator 810 to outside;

an UV lamp 200 formed on the periphery of the fine droplet spraying device 300 at regular intervals so as to irradiate an UV light on an object;

a camera 700 for automatically photographing a fingerprint when the fingerprint is developed on the object and storing a fingerprint image in a memory unit 830 according to a control of the controller 820;

the memory unit 830 for storing the fingerprint image photographed by the camera 700 therein;

an USB port 800 for transmitting the fingerprint image to an external terminal 900; and the controller 820 for controlling the vibrator 810, the fine droplet spraying device 300, the UV lamp 200, the camera 700, the memory unit 830, and the USB port 800.

The case 100 includes a front portion and a rear portion. A power supplying unit 500 for supplying the power to the developing reagent tank 600 for storing the developing liquid therein is formed on the rear portion thereof. Also, the camera 700, the UV lamp 200, and the fine droplet spraying device 300 are formed on the front portion thereof.

The vibrator 810 serves to vibrate the developing liquid, which is supplied from the developing reagent tank 600, according to the control of the controller, so that the fine droplets are sprayed through the fine droplet spraying device 300.

The fine droplet spraying device 300 is formed on the front portion of the case 100. The fine droplet spraying device 300 serves to discharge the fine droplets formed by the vibrator 810 to outside. That is, the fine droplet spraying device 300 serves to evenly spread the fine droplets on the object. Since the construction and techniques of discharging the fine droplets to outside are already well-known in the art, further descriptions on these are omitted here.

Also, the UV lamp 200 is formed on the periphery of the fine droplet spraying device 300 at regular intervals. The UV lamp 200 serves to irradiating the UV light on the object.

In the meantime, the UV lamp 200 includes a plurality of short wavelength lamps for generating a short wavelength wave and a plurality of long wavelength lamps for generating a long wavelength wave, which are properly arranged thereon.

For example, if there are four UV lamps, the UV lamp 200 includes two short wavelength UV lamps and two long wavelength UV lamps.

In the camera 700, when the fingerprint is developed on the object, it automatically photographs the fingerprint. Thereafter, the fingerprint image is stored in the memory unit 830 according to the control of the controller 820.

Also, the portable latent fingerprint developing apparatus according to the present invention further includes a camera switch (not shown) for operating the camera 700.

Since the camera 700 for automatically recognizing and photographing the fingerprint is already well-known in the art, a further description on this is omitted here.

In the memory unit 830, the fingerprint image photographed by the camera 700 is stored. Also, the USB port 800 is connected to the external terminal 900 and serves to transmit the fingerprint image to the external terminal 900.

Also, the controller 820 serves to control the vibrator 810, the fine droplet spraying device 300, the UV lamp 200, the camera 700, the memory unit 830, and the USB port 800.

According to an additional aspect of the present invention, the portable latent fingerprint developing apparatus according to one embodiment of the present invention further includes a spraying switch 400 for spraying the fine droplet and operating the UV lamp 200.

The spraying switch 400 includes one control button for spraying the fine droplet and another control button for operating the UV lamp 200. However, in case of only one control button, if it gives the button one press, the fine droplets are sprayed, meanwhile, if it gives the button another press, the UV lamp 200 can be operated.

For example, if the operator gives the spraying switch 400 one press, the controller 820 obtains the corresponding signal and transmits the operation signal to the vibrator 810. At this time, the developing liquid is vibrated through the vibrator 810 and then the fine droplets are sprayed through the fine droplet spraying device 300.

Simultaneously with the spray, the operation signal is transmitted to the UV lamp 200 by means of the controller 820, so that the UV lamp 200 is turned on.

Here, when the fingerprint is recognized, the operation signal is transmitted to the camera 700 by means of the controller 820, so that it can photograph the fingerprint image.

That is, the UV light is irradiated on the object simultaneously with the spray at the scene of the crime, so that the fingerprint can be seen with the naked eye. Simultaneously, it photographs the fingerprint image and the corresponding image is stored in the memory unit 830.

In addition, since the latent fingerprint is directly photographed by the camera 700, the latent fingerprint images can be stored in real time without a separate manipulation.

Here, the UV lamp 200 should be electrically connected to the camera 700. Since the method of the power supply is already well-known in the art, a further description on this is omitted here.

In the meantime, as shown in FIG. 4, there are a manner using the general sprayer and a manner of irradiating the UV lamp in the conventional fingerprint recognition technology. However, in the present invention, since the UV light is irradiated on the object simultaneously with the spray, the present invention is superior to the conventional art in terms of the effect of the fingerprint developing.

The UV lamp 200 and the fine droplet spraying device 300 face in the same direction so as to spray the fine droplets of the developing liquid and irradiate the UV light of the UV lamp toward the same area, thereby detecting the fingerprint image simultaneously with the spray thereof.

The developing reagent tank 600 includes a separate stopper for storing the fingerprint developing liquid therein and opening and closing the developing reagent tank 600.

The fine droplet spraying device 300 includes a plurality of small apertures for discharging the fine droplets formed by the vibrator 810 to outside.

Also, the UV lamp 200 is formed on the periphery of the fine droplet spraying device 300 at regular intervals and includes a plurality of UV LEDs for irradiating the UV light on the object.

In the meantime, according to an additional aspect of the present invention, the portable latent fingerprint developing apparatus according to one embodiment of the present invention further includes a fingerprint image discriminating unit for recognizing and discriminating the fingerprint images so as to obtain the images through the camera 700 continually operated and automatically recognize the fingerprint images, thereby storing the fingerprint images in the memory unit 830.

Also, in the present invention, if the spraying switch 400 is pressed, the UV lamp 200 is operated simultaneously with the spray thereof.

Figure 9:
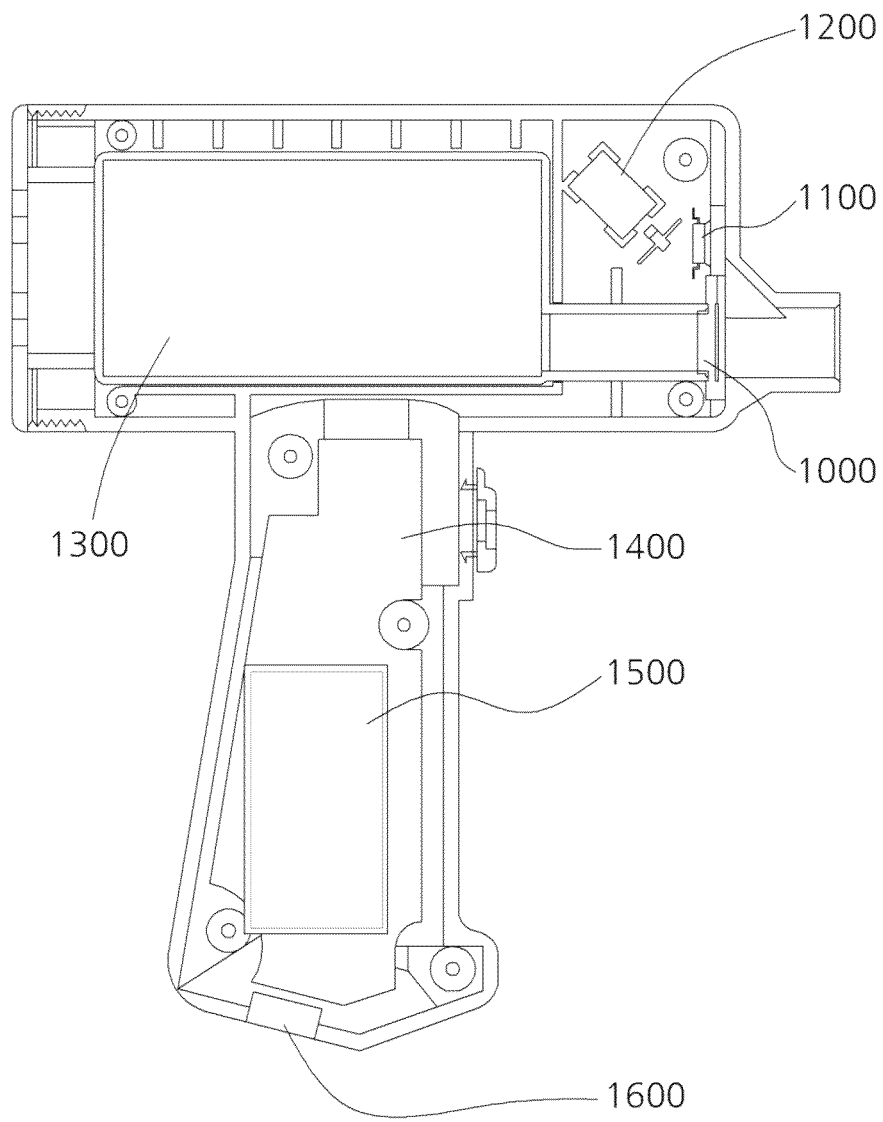
FIG. 9 is a perspective view illustrating a portable latent fingerprint developing apparatus according to another embodiment of the present invention.

FIG. 9 is a perspective view illustrating a portable latent fingerprint developing apparatus according to another embodiment of the present invention.

As shown in FIG. 9, the portable latent fingerprint developing apparatus according to another embodiment of the present invention is a gun type portable latent fingerprint developing apparatus.

That is, the portable latent fingerprint developing apparatus according to another embodiment of the present invention includes:

an ultrasonic vibrator 1000 for vibrating a developing liquid supplied from a developing reagent tank 1300 and spraying fine droplets;

an UV lamp 1100 for irradiating an UV light on an object a small motor 1200 for operating a fan (not shown) during spraying thereof formed on an upper portion of the UV lamp 1100;

the developing reagent tank 1300 formed at a center of a case;

a PCB 24 PIN connector 1400 formed at an inside of a lower grip;

a lithium ion battery 1500 formed at an upper end of the PCB 24 PIN connector 1400; and a rechargeable 24 PIN connection port 1600 for charging the lithium ion battery 1500 formed at a lower end of the case.

That is, the ultrasonic vibrator 1000 is formed at the front portion thereof, the UV lamp 1100 is formed at the upper portion thereof, and the small motor 1200 for operating the fan (not shown) is formed on the uppermost portion thereof.

Also, the developing reagent tank 1300 is formed at the center of the body case, the PCB 24 PIN connector 1400 is formed at the inside of the lower grip, and the lithium ion battery 1500 is formed at the upper end of the PCB 24 PIN connector 1400.

In the meantime, the rechargeable 24 PIN connection port 1600 is formed at the lower end of the body case, so that the lithium ion battery 1500 can be charged as necessary.

As described above, the portable latent fingerprint developing apparatus according to the present invention may be a cellular phone type portable latent fingerprint developing apparatus or a gun type portable latent fingerprint developing apparatus.

In case of the latent fingerprint developing liquid, a talc, a mica, and a silica etc. can be utilized as the extender filler.

Also, compressive type powders such as a white color powder of a titanium oxide, a barium sulfate, and a calcium carbonate and a black color power of carbon black, graphite, and a molybdenum disulfide etc. can be utilized as the color pigment.

As described above, the portable latent fingerprint developing apparatus according to the present invention can visibly check out an external shape of a finger print by using an UV LED lamp, after a fine spray of a fingerprint developing liquid is conducted by using a vibrator and provide the corresponding fingerprint image to an external terminal, after it is photographed by a camera.

Also, the fine spray can be conducted without spraying or applying the fingerprint developing liquid and it shines the UV LED light simultaneously with the spraying of the fingerprint developing liquid, so that it can be sprayed in a wide space and the fingerprint image can be directly detected.

Moreover, the portable latent fingerprint developing apparatus can provide the convenient portability and storage to users.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A portable latent fingerprint developing apparatus, comprising:
    a case;
    a developing reagent tank disposed inside the case for storing a developing liquid therein;
    a vibrator vibrating the developing liquid supplied from the developing reagent tank to form fine droplets according to a control of a controller;
    a fine droplet spraying device disposed in a front side of the case and including a plurality of small apertures for discharging the fine droplets formed by the vibrator toward an object bearing a fingerprint;
    an UV lamp including a plurality of UV LEDs for irradiating an UV light on the object, the plurality of UV LEDs being disposed spaced at uniform intervals on the periphery of the fine droplet spraying device; and
    a camera disposed in the front side of the case for photographing the fingerprint when the fingerprint is developed on the object; and
    the controller for controlling the portable latent fingerprint developing apparatus.

2. The portable latent fingerprint developing apparatus as claimed in claim 1, wherein the UV lamp and the fine droplet spraying device face in the same direction so as to spray the fine droplets of the developing liquid and irradiate the UV light of the UV lamp toward the same area, thereby detecting the fingerprint image simultaneously with the spray thereof.

3. The portable latent fingerprint developing apparatus as claimed in claim 1, wherein the developing reagent tank comprises a separate stopper formed at a rear portion of the case so as to store the fingerprint developing liquid therein and open and close the developing reagent tank.

4. The portable latent fingerprint developing apparatus as claimed in claim 1, further comprising: and
    a memory unit for storing the fingerprint image photographed by the camera therein.

5. The portable latent fingerprint developing apparatus as claimed in claim 4, further comprising a fingerprint image discriminating unit for recognizing and discriminating the fingerprint images so as to obtain the images through the camera continually operated and automatically recognize the fingerprint images, thereby storing the fingerprint images in the memory unit.

6. The portable latent fingerprint developing apparatus as claimed in claim 1, further comprising an USB port for transmitting the fingerprint image to an external terminal.

7. The portable latent fingerprint developing apparatus as claimed in claim 1, further comprising a spraying switch for spraying the fine droplet.

8. The portable latent fingerprint developing apparatus as claimed in claim 7, wherein the spraying switch is configured such that when pressed, the UV lamp is simultaneously operated therewith.

9. The portable latent fingerprint developing apparatus as claimed in claim 1, wherein the UV lamp is electrically connected to the camera.

10. The portable latent fingerprint developing apparatus as claimed in claim 1, further comprising: a power supplying unit formed on one side of a rear portion thereof so as to supply a power thereto.

11. The portable latent fingerprint developing apparatus as claimed in claim 1, wherein the UV lamp comprises a plurality of short wavelength lamps for generating a short wavelength wave and a plurality of long wavelength lamps for generating a long wavelength wave.

12. A portable latent fingerprint developing apparatus, comprising:
- a case;
- a developing reagent tank disposed inside the case so as to store a developing liquid therein;
- a vibrator vibrating the developing liquid supplied from the developing reagent tank to form fine droplets according to a control of a controller;
- a fine droplet spraying device formed on a front side of the case and including a plurality of small apertures so as to discharge the fine droplets formed by the vibrator toward an object bearing a fingerprint;
- an UV lamp including a plurality of UV LEDs formed spaced at uniform intervals on the periphery of the fine droplet spraying device so as to irradiate an UV light on the object;
- a camera disposed in the front side of the case for automatically photographing the fingerprint when the fingerprint is developed on the object;
- a memory unit for storing the fingerprint image photographed by the camera therein;
- an USB port for transmitting the fingerprint image to an external terminal;
- a spraying switch for spraying the fine droplet and operating the UV lamp; and
- the controller for controlling the vibrator, the fine droplet spraying device, the UV lamp, the camera, the memory unit, the USB port, and the spraying switch.

13. The portable latent fingerprint developing apparatus as claimed in claim 12, further comprising: a camera switch for operating the camera.

14. The portable latent fingerprint developing apparatus as claimed in claim 12, wherein the UV lamp is electrically connected to the camera.

15. The portable latent fingerprint developing apparatus as claimed in claim 12, further comprising: a power supplying unit formed on one side of a rear portion thereof so as to supply a power thereto.

16. The portable latent fingerprint developing apparatus as claimed in claim 12, wherein the UV lamp comprises a plurality of short wavelength lamps for generating a short wavelength wave and a plurality of long wavelength lamps for generating a long wavelength wave.

* * * * *